Figure 1:
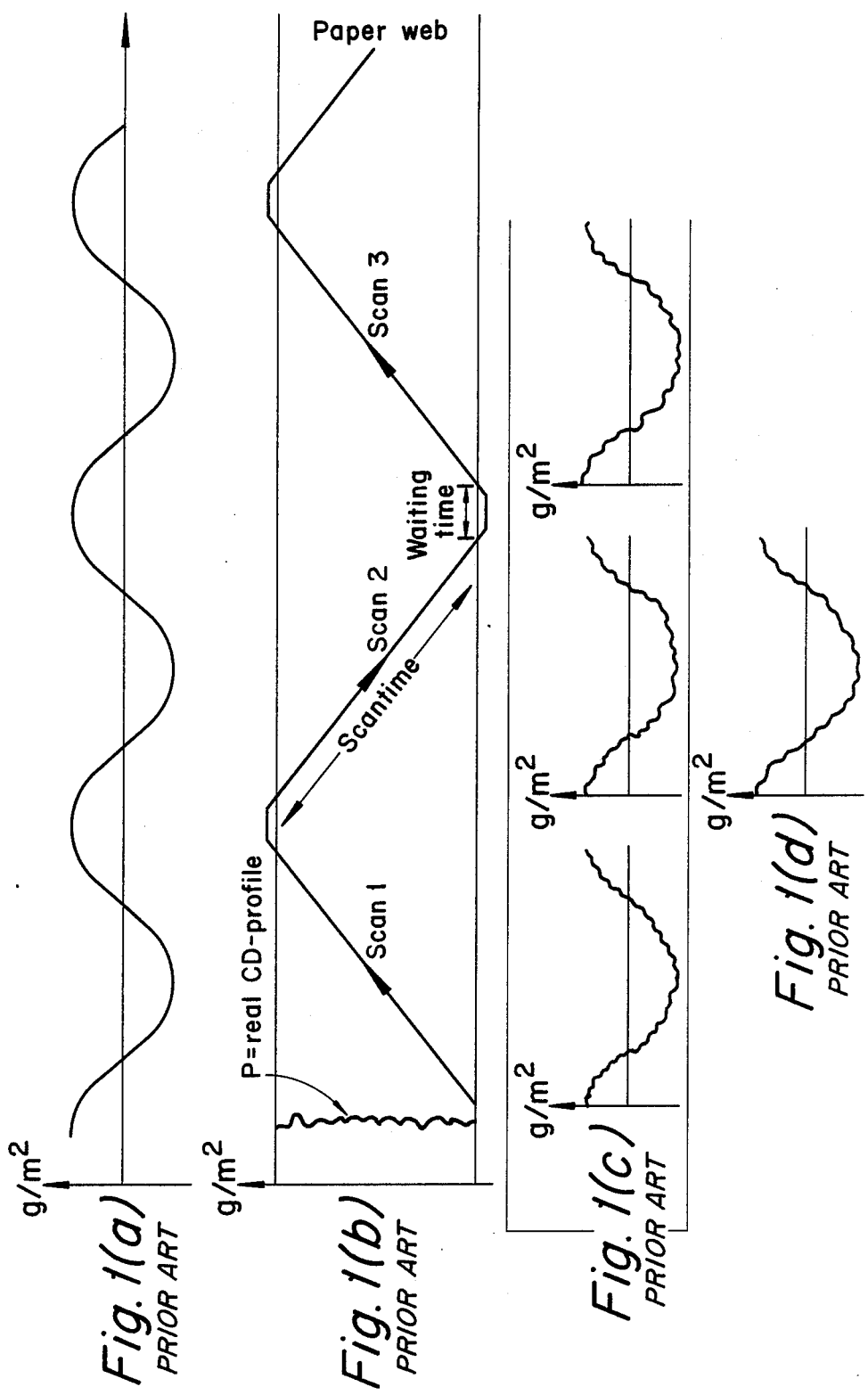

United States Patent [19]
Östman

[11] Patent Number: 4,939,929
[45] Date of Patent: Jul. 10, 1990

[54] MEASUREMENT OF THE PROPERTIES OF A WEB IN PAPER PRODUCTION

[75] Inventor: Leif T. Östman, Spånga, Sweden

[73] Assignee: STFI, Stockholm, Sweden

[21] Appl. No.: 281,386

[22] Filed: Dec. 8, 1988

[51] Int. Cl.⁵ .................. G01N 33/34; G01N 33/44
[52] U.S. Cl. ........................... 73/159; 73/73; 356/431; 250/563; 364/568; 364/471; 364/473
[58] Field of Search .............. 73/159, 73; 356/238, 356/429, 430, 431; 250/563, 252.1 A; 364/568, 471, 473

[56] References Cited

U.S. PATENT DOCUMENTS

| | | | |
|---|---|---|---|
| 3,000,438 | 9/1961 | Alexander | 73/159 |
| 3,332,279 | 7/1967 | Tompos et al. | 73/73 |
| 3,508,035 | 4/1970 | Worthley | 364/568 |
| 3,552,203 | 1/1971 | Freeh | 73/159 |
| 3,562,500 | 2/1971 | Grant | 364/568 |
| 3,610,899 | 10/1971 | Dahlin | 73/73 |
| 3,612,839 | 10/1971 | DeWitt et al. | 73/73 |
| 3,666,621 | 5/1972 | Adams | 364/568 |
| 3,914,585 | 10/1975 | Wilhelm, Jr. et al. | 73/159 |
| 4,000,402 | 12/1976 | Higham | 364/469 |
| 4,453,404 | 6/1984 | Powell et al. | 73/159 |
| 4,476,717 | 10/1984 | Murphy | 73/159 |

Primary Examiner—William A. Cuchlinski, Jr.
Assistant Examiner—Diego F. F. Gutierrez
Attorney, Agent, or Firm—Burns, Doane, Swecker & Mathis

[57] ABSTRACT

Variations in the properties of a continuously running web are measured by reciprocating the scanning device across the web. The movement of the scanning device is so time controlled that this movement is out of phase with the variation in the paper properties in the machine direction of the web.

6 Claims, 2 Drawing Sheets

MEASUREMENT OF THE PROPERTIES OF A WEB IN PAPER PRODUCTION

This invention relates to the measuring of variations in the properties of a continuously running paper web. The variations in the properties of a web usually are determined by means of a scanning device, a so-called traversing meter, which is reciprocated over the web while the web is moving continuously. By this scanning device different properties of the web, for example grammage and moisture content, are measured, which properties can vary both in the cross-direction and longitudinal direction of the web. In order to obtain acceptable information on the properties of the web and the variations thereof, several traversing movements are carried out. From these measurements, mean value formation, exponential filtering or other calculation is made in order to compensate for errors, which arise due to the fact, that the measurement does not take place perpendicularly across the web, but obliquely as a consequence of the web movement.

However, certain periodically recurring variations in properties in the longitudinal direction (machine direction profile) of the web, for example, still can affect the values measured for the cross properties in an unfavourable way. Irrespective of how the measured cross properties (cross direction profiles) are utilized in the mean value formation or other calculation, an incorrect cross direction profile can be indicated. By investigating different periodical variations in the machine direction profile, which can affect the indication of the real cross direction profile, one finds that a number of variations in the machine direction profile cannot be filtered out, but are included as disturbances in the cross direction profile. This phenomenon usually is called tuck.

A corresponding situation can arise at the indication of the machine direction profile, due to the fact that periodical variations in the cross direction profile affect the indication of the real machine direction profile.

It was tried in different ways to evade the aforesaid problems, for example by more rapid traversing, improved filtering and other statistic formation at the calculation of the profile or zone division of the web for a more rapid indication of the machine direction profile. Such measures certainly have reduced the problems to a certain extent, but did not bring about a solution of the problems.

According to the present invention, the aforesaid problems are solved by time controlling the movement of the scanning device so that this movement is out of phase with the periodical variation of the paper properties in the longitudinal direction of the web.

Figure 2:
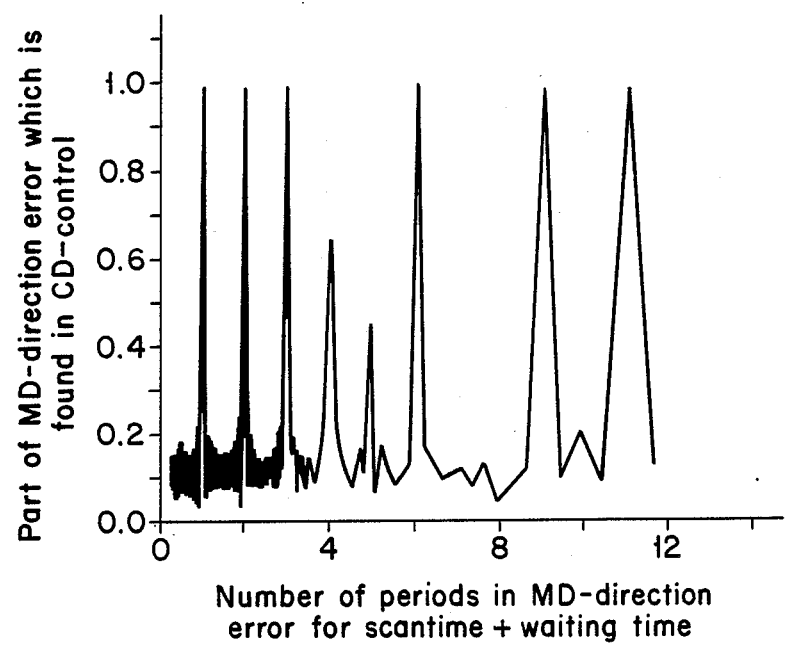
Figure 3:
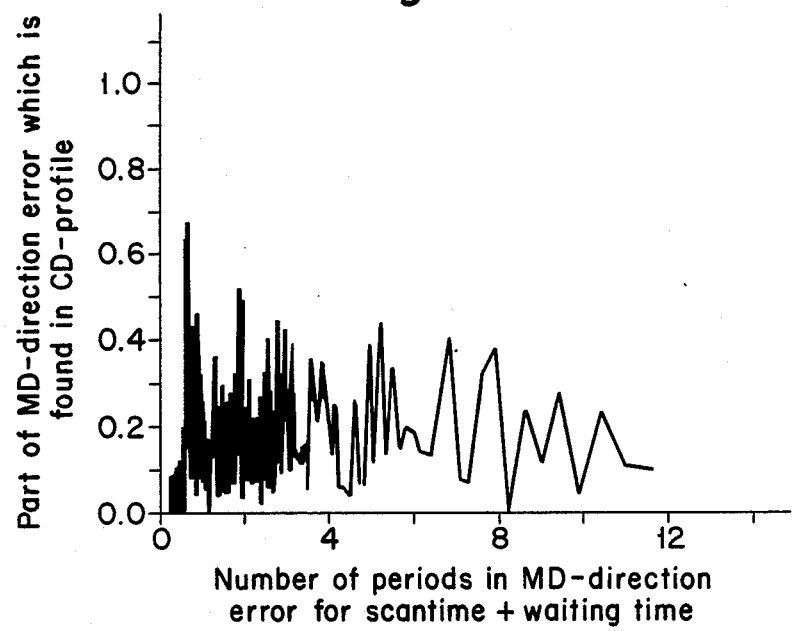

The invention is described in greater detail in the following with reference to the accompanying drawings, in which FIG. 1 shows how periodical variations in the machine direction profile affect the cross direction profile, FIG. 2 shows how much of the longitudinal disturbance for different lengths of periods remain in a mean value of 20 cross direction profiles when the method according to the invention is not used, FIG. 3 shows the same as FIG. 2 when the method according to the invention is used, FIG. 4 shows schematically a device for carrying out the method according to the invention.

The invention can be applied to all types of traversing meters.

The scanning device 1 shown in FIG. 4 comprises a measuring frame 2 with a measured value transmitter 3. An electronic control device 4 is arranged to control the movement of the measured value transmitter in the measuring frame 2 across the web 5. At the measurement the properties of the web are indicated along the dashed line 6.

In FIG. 1, the diagram (a) shows a periodical disturbance in the grammage ($g/m^2$) in the longitudinal direction in a web. Diagram (b) corresponds to diagram (a) and shows how a traversing meter passes over the web. The traversing movements are carried out at a constant speed and are marked "scan 1", "scan 2" and "scan 3". The real cross direction profile, P, of the web is shown to the left in the diagram. Diagram (c) shows the profiles measured by the meter at the respective traversing movement. Diagram (d) shows a mean value of the profiles in diagram (c). Owing to the periodical disturbance in the machine direction profile, the measured cross direction profile does not represent in this case the real cross direction profile.

It was found that the periodical disturbance in the longitudinal direction affects the measured cross direction profile and distorts it, irrespective of filtering and mean value formation, as long as the traversing is carried out in conventional manner. By moving the scanning device out of phase with the periodical disturbances in the longitudinal direction, it was found possible to minimize the distortion of the measured cross direction profile in relation to the real one. The scanning device, thus, can be moved with varying speed and/or with varying idle times in the turning points.

EXAMPLE

The measurement of the cross direction profile of a web was carried out with a traversing meter of conventional type.

The measurements first were made in a normal manner, i.e. with the time of 30 seconds for each traversing and an idle time of 3 seconds in the turning points.

A mean value for the cross direction profile was calculated for 20 traversings. It was calculated for different periodicity of the periodical disturbances in the longitudinal direction, how these affected the measured cross direction profile.

FIG. 2 shows the result of these measurements. The proportion of remaining disturbance in the cross direction profile was noted as a function of the number of periods in the machine direction profile during the traversing time.

The measurements were thereafter repeated, with the difference that the idle time of the meter in the turning points was varied. The idle times were changed according to a cycle recurring after 20 traversings as follows

| Traversing (No) | Idle time (sec) | Traversing (No) | Idle time (sec) |
| --- | --- | --- | --- |
| 1 | 3 | 11 | 9 |
| 2 | 4 | 12 | 8 |
| 3 | 5 | 13 | 8 |
| 4 | 6 | 14 | 7 |
| 5 | 7 | 15 | 7 |
| 6 | 7 | 16 | 6 |
| 7 | 8 | 17 | 5 |
| 8 | 8 | 18 | 4 |
| 9 | 9 | 19 | 3 |
| 10 | 9 | 20 | 3 |

The result thereof is shown in FIG. 3. As in FIG. 2, the proportion of remaining disturbance in the cross direction profile has been noted as a function of the number of periods in the machine direction profile disturbance during the traversing time.

A comparison of these results shows that the effect of the longitudinal disturbances on the measured cross direction profile has been reduced substantially by varying the idle time of the meter in the turning points.

The reason of this is that the movement of the meter is out of phase with the periodical variation in the web profile in the longitudinal direction. For obtaining this difference in phase, also other methods can be imagined. The idle times of the meter in the turning points can be varied in different ways. During 10 traversings, for example, an idle time corresponding to 1 traversing can be applied (in which case the total time will be 11 traversings).

The desired difference in phase also can be obtained by varying the meter speed during the traversing. The exact way of moving the scanning device over the web depends, in part on the type of filtering used for calculating the cross direction profile.

The invention, of course, is not restricted to the embodiments shown, but can be varied within the scope of the invention idea.

I claim:
1. A method of measuring variations in the properties of a continuously running paper web comprising indication of the paper properties by reciprocating a scanning device across the web, wherein movement of the scanning device is time controlled, so that said movement is out of phase with periodical variation of the paper properties in the longitudinal direction of the web.
2. A method as defined in claim 1, wherein the time control is carried out so that the movement of the scanning device also is out of phase with the variation of the paper properties in the cross direction of the web.
3. A method as defined in claim 1, wherein the time control is carried out by varying the idle time of the scanning device between the movements across the web.
4. A method as defined in claim 1, wherein the time control is carried out by varying the speed of the scanning device across the web.
5. A method as defined in claim 2, wherein the time control is carried out by varying the idle time of the scanning device between the movements across the web.
6. A method as defined in claim 2, wherein the time control is carried out by varying the speed of the scanning device across the web.